United States Patent [19]

Mäder et al.

[11] Patent Number: 4,711,375
[45] Date of Patent: Dec. 8, 1987

[54] DEVICE FOR TREATING BURN AND SCALD WOUNDS

[75] Inventors: Karl Mäder, Pfaffikon; Guido Schönenberger, Reinach; Carlo A. Buzzi, Zurich, all of Switzerland

[73] Assignee: IDC-Chemie AG, Zurich, Switzerland

[21] Appl. No.: 856,990

[22] Filed: Apr. 29, 1986

[30] Foreign Application Priority Data

May 17, 1985 [CH] Switzerland .......................... 2123/85

[51] Int. Cl.⁴ .............................................. B67D 5/52
[52] U.S. Cl. ..................... 222/135; 604/289; 604/23; 128/200.19; 128/200.23; 222/183; 222/402.13; 222/321
[58] Field of Search ............... 222/135, 129, 182, 183, 222/402.13, 402.1; 239/304, 303, 305; 604/310, 289, 191, 23; 128/200.19, 200.23

[56] References Cited

U.S. PATENT DOCUMENTS

| 638,481 | 12/1899 | Seltzer. | |
|---|---|---|---|
| 1,614,532 | 1/1927 | Mobley | 128/200.19 |
| 3,269,605 | 8/1966 | Silver | 222/135 |
| 3,278,086 | 10/1966 | Clouzeau et al. | 222/135 |
| 3,349,967 | 10/1967 | Schneller | 222/135 |
| 3,366,279 | 1/1968 | Parker et al. | 222/135 |
| 3,383,879 | 5/1968 | Tice | 222/402.13 |
| 3,451,593 | 6/1969 | Dillarstone | 222/135 |
| 3,508,684 | 4/1970 | Grech | 222/129 |
| 3,936,000 | 2/1976 | Weyn | 222/402.13 |

FOREIGN PATENT DOCUMENTS

| WO84/04883 | 12/1984 | PCT Int'l Appl. . |
| 1104214 | 2/1968 | United Kingdom . |
| 1162790 | 8/1969 | United Kingdom . |

*Primary Examiner*—H. Grant Skaggs
*Attorney, Agent, or Firm*—Kinzer, Plyer, Dorn, McEachran & Jambor

[57] ABSTRACT

This device includes a water container (1) with a pump (8), an operating button (4) and a spray nozzle (5). A second container (2) holds a refrigerant which is released through a second spray nozzle (7) by pressing on a second button (24). As a first aid measure, a film of water is first sprayed on the burn wound and then is frozen by means of the refrigerant. In this way, an immediate and drastic reduction in pain is achieved. Since the heat is rapidly and effectively dissipated from the injured tissue, substantially fewer burn toxins are formed so the healing prospects are greatly improved. The subsequent scar tissue formation on the wound is much better from a cosmetic standpoint. This device may be constructed in a small and handy form and therefore can be kept ready to use wherever there is the risk of burn and scald wounds.

1 Claim, 2 Drawing Figures

DEVICE FOR TREATING BURN AND SCALD WOUNDS

It has been found that even when the patient's condition has stabilized after severe burn wounds, serious infections often occur, sometimes with lethal consequences. It has also been found that toxic substances (burn toxins) which develop due to the heat generated in the skin are the underlying cause for the fatal progress of burn traumas. These toxic substances formed by thermal decomposition of proteins weaken the immune defense so the body is no longer able to resist the unavoidable invasion of baceteria through the large area wounds.

It has been found that immediate cooling, i.e,. within 30 to 60 seconds, of the burn wound with cold water is very favorable in several regards. First the pain is reduced and the decomposition of proteins and the development of burn toxins is greatly reduced or eliminated. The wound heals considerably more rapidly and scarring is less problematical.

However, cold water is often not available rapidly as a first aid measure. This invention is based on the goal of eliminating this shortcoming. This problem is solved by the invention defined in claim 1.

This invention provides a device which can be made available for easy access and use wherever there is the risk of burn or scald injuries. By separating the agents into two containers, the liquid to be applied (preferably water) can be kept germ-free with a long shelf-life. The liquid cooled by the coolant has a relatively high cooling capacity, so it is capable of cooling the burn wound for a sufficiently long period of time. This is in contrast with commercial refrigerant sprays which evaporate rapidly and therefore permit only superficial cooling. With the cold sprays, the water is preferably frozen to an ice layer after application. This substantially increases the long-term effect of cooling because ice has a very high cooling capacity.

Claim 1 is differentiated with respect to U.S. Pat. No. 3,366,279. This device has two liquid containers and a common valve which sprays liquid optionally from one or the other container. What is intended there is especially paint sprays, where a primer layer can be applied first and then a top coat is applied with the same unit. For medical purposes, first an antiseptic agent is applied and then a film coating.

Practical examples of this invention are explained below with reference to the figure.

Figure 1:
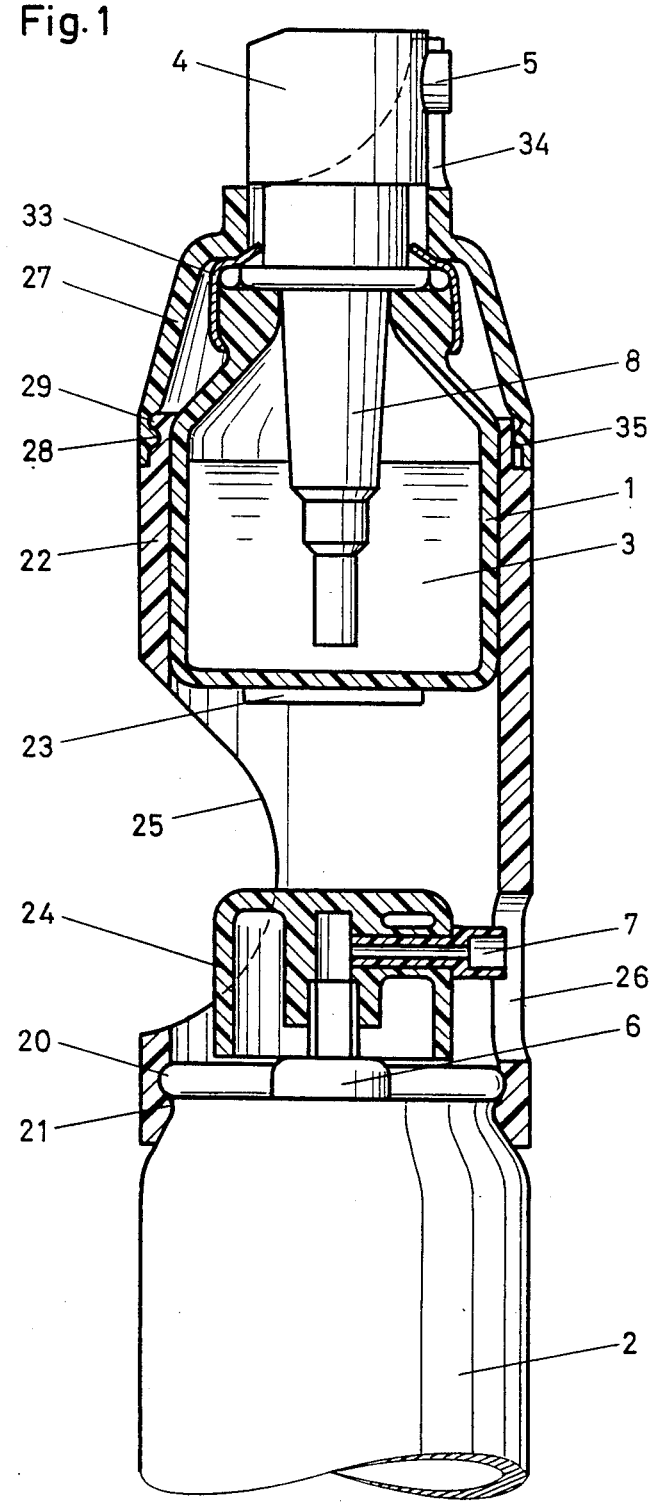
FIG. 1 shows an axial section of a first version.

In the version according to FIG. 1, the two containers 1 and 2 are positioned coaxially one above the other. Container 1 holds sterile water 3 and is considerably smaller than container 2 which holds a refrigerant such as $Cl_2F_2$. A housing 22 is snapped onto a flanged edge 20 of container 2 by means of a ring-shaped projection 21. The housing has a cylindrical hole and an axial stop 23 to receive container 1. To operate a button 24 of valve 6 of container 2, housing 22 has an access opening 25. Diametrically opposite the access opening 25, housing 22 has an elongated hole 26 into which spray nozzle 7 of valve 6 projects. Container 1 is held in housing 22 by a snap-on guide cap 27. This engages a projection 29 of housing 22 with a ring-shaped projection 28. A pump 8 that projects to the base of container 1 is mounted on container 1 by means of a flanged crown 33 so that it is airtight. The spring-loaded operating button 4 of pump 8 has a spray nozzle 5 which is guided in an axial slit 34 of guide cap 27. Guide cap 27 has a projection 35 which engages an axial groove of the housing 22 so that slit 34 is flush with the elongated hole 26 and thus the two spray nozzles 5 and 7 are aligned in parallel.

The water 3 in container 1 remains sterile for a long period of time because of the airtight seal of container 1. Pump 8 guarantees safe and reliable operation of the device even after years of storage. Instead of pump 8, however, bubble storage would also be possible, where the water would be separated from a propellant gas by a membrane.

In using the device described here, first water is sprayed on the burn wound by pressing on button 4. Then this water film is frozen by a stream of refrigerant from spray nozzle 7 by pressing on button 24, so the burn wound is effectively cooled without damaging the tissue due to excessively low temperatures. The cooling effect lasts for a longer period of time due to the great cooling capacity of the ice. It is advisable to repeat the treatment after about 20 minutes, or in the case of severe burns, to repeat it several times at longer intervals. The treatment described here is a first aid measure and does not replace treatment by a physician, but it does assure substantially greater prospects of success.

Figure 2:
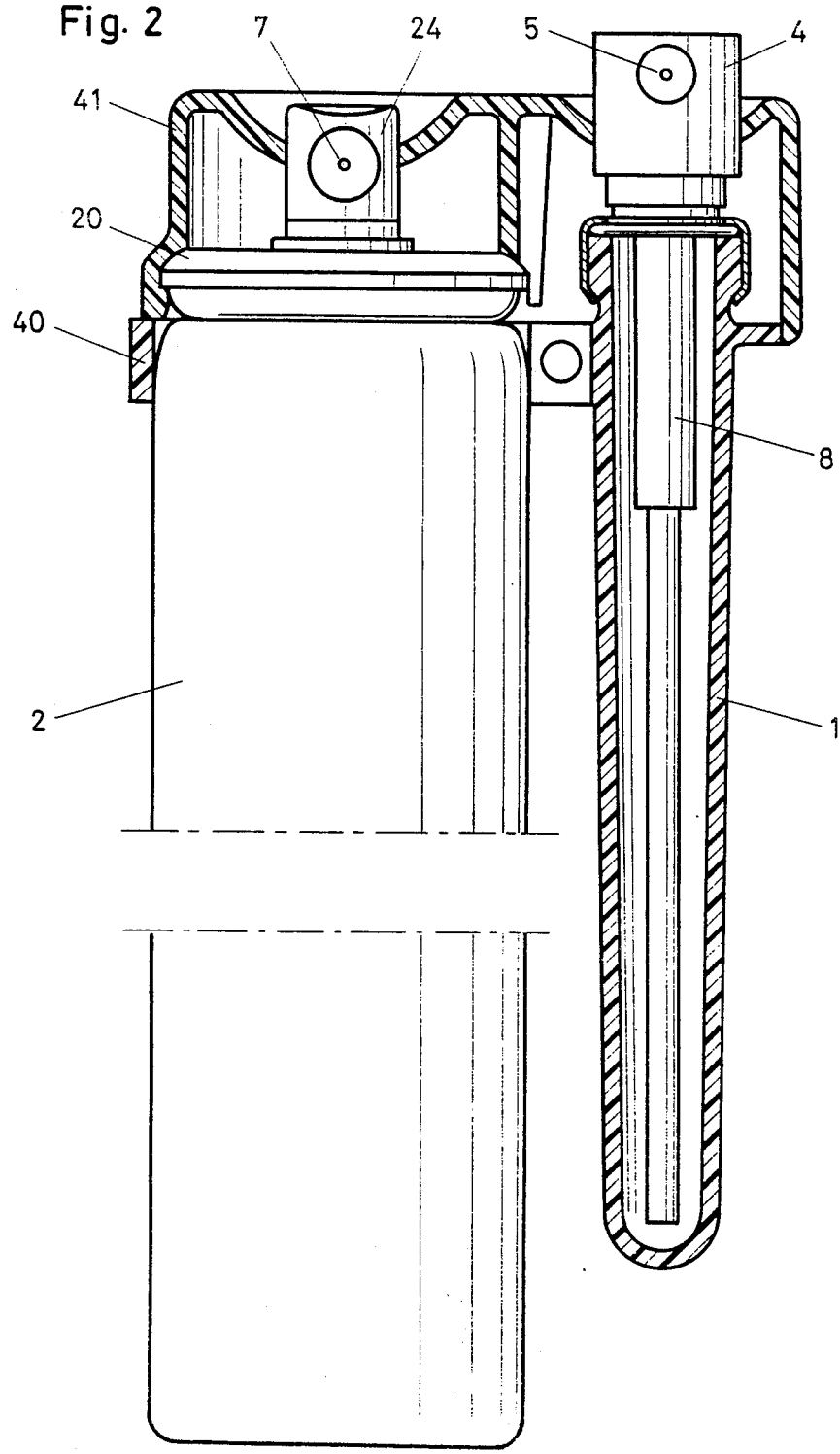
FIG. 2 shows a frontal view of a second version.

In the version according to FIG. 2, the two containers 1 and 2 are side by side. Container 1 is part of housing 40 which is placed on container 2 and is secured by a guide cap 41 snapped on the flanged edge 20 of container 2. The guide cap 41 has a guide slit for guiding the two spray nozzles 5 and 7, like the guide slit 34 in the version according to FIG. 1.

Fluorocarbons which are neither flammable nor toxic and do not cause any irritation of the mucosa are especially suitable refrigerants. Such compounds are known as safety refrigerants. Especially suitable is dichlorodifluoromethane ($CCl_2F_2$) and/or chlorodifluoromethane ($CHClF_2$) with boiling points of $-29.8°$ C. and $-40.8°$ C. at 1 bar. To adjust the vapor pressure and thus also the refrigeration effect, $CCl_2F_2$ and/or $CHClF_2$ may also be mixed with $CCl_3F$, $CClF_2F$ or with $CClF_2$-$CClF_2$.

We claim:

1. A device for treating burn and scald wounds comprising:
   a first container (1) which contains water (3) and has an operating button (4) of a pump (8), with a first spray nozzle (5) for spraying the water;
   a second container (2) which contains a coolant and has a separate valve (6) with a second spray nozzle (7) which is aligned approximately parallel with the first spray nozzle;
   a housing (22) connecting the first and second containers in coaxial relation with the first container positioned above the valve (6) of the second container, the housing snapping onto the second container and the housing having an access opening (25) for operating the valve (6) and a slit opening (26) diametrically opposite the access opening (25), the second spray nozzle projecting into the slit opening (26); and
   a snap-on guide cap (27) holding the first container (1) in the housing (22) and having a guide slit (34) into which the first spray nozzle (5) projects, the guide slit (34) being aligned with the slit opening (26).

* * * * *